(12) United States Patent
Buie et al.

(10) Patent No.: US 8,864,647 B2
(45) Date of Patent: Oct. 21, 2014

(54) INCONTINENCE TREATMENT DEVICE WITH PUBIC ARM ATTACHMENT MECHANISM

(75) Inventors: Mitiku Buie, Minneapolis, MN (US); Christopher Deegan, St. Paul, MN (US); Nicholas Ellering, Crystal, MN (US); Pornpimon Ongmorakot, St. Paul, MN (US)

(73) Assignee: Coloplast A/S, Humlebaek (DK)

( * ) Notice: Subject to any disclaimer, the term of this patent is extended or adjusted under 35 U.S.C. 154(b) by 216 days.

(21) Appl. No.: 13/214,265

(22) Filed: Aug. 22, 2011

(65) Prior Publication Data

US 2013/0046132 A1 Feb. 21, 2013

(30) Foreign Application Priority Data

Aug. 19, 2011 (DK) .................................. 2011 70458

(51) Int. Cl.
*A61F 2/02* (2006.01)
*A61F 2/00* (2006.01)

(52) U.S. Cl.
CPC .................................. *A61F 2/0045* (2013.01)
USPC ........................................................ 600/30

(58) Field of Classification Search
CPC ... A61F 2/0004; A61F 2/0031; A61F 2/0036; A61F 2/0045; A61B 2017/00805
USPC ...................................... 600/30, 37; 606/151
See application file for complete search history.

(56) References Cited

U.S. PATENT DOCUMENTS

| | | | | |
|---|---|---|---|---|
| 7,431,690 B2 * | 10/2008 | Merade et al. | ................... | 600/30 |
| 2002/0028980 A1 * | 3/2002 | Thierfelder et al. | ............ | 600/37 |
| 2002/0128670 A1 * | 9/2002 | Ulmsten et al. | ............... | 606/151 |
| 2003/0023137 A1 | 1/2003 | Gellman | | |
| 2005/0085688 A1 * | 4/2005 | Girard et al. | .................... | 600/37 |
| 2006/0122457 A1 | 6/2006 | Kovac et al. | | |
| 2006/0134159 A1 | 6/2006 | Nicita | | |
| 2008/0300607 A1 * | 12/2008 | Meade et al. | ................. | 606/119 |
| 2009/0012351 A1 * | 1/2009 | Anderson et al. | ............... | 600/30 |

(Continued)

FOREIGN PATENT DOCUMENTS

WO 2004012626 A1 2/2004
WO 2004045457 6/2004

(Continued)

OTHER PUBLICATIONS

ISR and Written Opinion from EPO dated Oct. 26, 2012 attached.

(Continued)

*Primary Examiner* — Jacqueline Cheng
*Assistant Examiner* — Kaylee Wilson
(74) *Attorney, Agent, or Firm* — Coloplast Corp., Coloplast A/S; Nick Baumann

(57) ABSTRACT

An implant includes a support body defining a longitudinal axis, two transverse arms, two pubic arms, and a pubic arm attachment mechanism. The two transverse arms are aligned on a common transverse axis of the implant. The two pubic arms include a first pubic arm spaced a distance apart from a second pubic arm and both the first and second pubic arms are parallel to the longitudinal axis. The pubic arm attachment mechanism is attached to an end of each of the first and second pubic arms. Each of the first and second pubic arms has an arm length that is less than a body length of the support body.

20 Claims, 7 Drawing Sheets

(56) References Cited

U.S. PATENT DOCUMENTS

| | | |
|---|---|---|
| 2009/0171142 A1 | 7/2009 | Chu |
| 2010/0191038 A1 | 7/2010 | Kubalak et al. |
| 2010/0197999 A1 | 8/2010 | Deegan et al. |
| 2014/0039244 A1 | 2/2014 | Browning |
| 2014/0039248 A1 | 2/2014 | Browning |
| 2014/0051917 A1 | 2/2014 | Browning |

FOREIGN PATENT DOCUMENTS

| | | |
|---|---|---|
| WO | 2004091442 A2 | 10/2004 |
| WO | 2006041861 A2 | 4/2006 |
| WO | 2007118260 A1 | 10/2007 |
| WO | 2008152435 A1 | 12/2008 |

OTHER PUBLICATIONS

Office Action mailed on Mar. 19, 2013 in U.S. Appl. No. 13/430,761. The Office Action is provided since this reference is stored on the Office IFW.

Office Action mailed on Jul. 18, 2013 in U.S. Appl. No. 13/430,761. The Office Action is provided since this reference is stored on the Office IFW.

Office Action mailed on Aug. 14, 2014 in U.S. Appl. No. 13/430,761. The Office Action is provided since this reference is stored on the Office IFW.

* cited by examiner

INCONTINENCE TREATMENT DEVICE WITH PUBIC ARM ATTACHMENT MECHANISM

BACKGROUND

Urinary incontinence is the undesired leakage of urine from the bladder and this malady affects both men and women, with some estimates as high as 30% of the population experiencing some level of urinary incontinence.

Devices for treating urinary incontinence include slings, supports, and other devices that are implanted in a patient's body to support, elevate, or compress the urethra. A urethral support is a urinary incontinence treatment device that is surgically implanted under the urethra to inhibit urine from undesirably exiting the urethra, particularly during a provocative event such as when coughing or sneezing.

Other urinary incontinence treatment devices include artificial sphincters that selectively coapt the urethra and injected bulking liquids that are applied alongside a layer of the urethra to support or partially coaptate the urethra.

Improved incontinence treatment methods and devices would be welcomed by both the patient and the surgical staff.

SUMMARY

One aspect provides an implant adapted to treat urinary incontinence. The implant includes a support body defining a longitudinal axis, two transverse arms, two pubic arms, and a pubic arm attachment mechanism. The two transverse arms include a first arm extending from the support body transverse to the longitudinal axis and a second arm extending from the support body in a direction opposite the first arm and transverse to the longitudinal axis such that the first and second arms provide transverse arms that are aligned on a common transverse axis of the implant. The two pubic arms include a first pubic arm extending from the support body and a second pubic arm extending from the support body, with the first pubic arm spaced a distance apart from the second pubic arm and both the first and second pubic arms parallel to the longitudinal axis. The pubic arm attachment mechanism is attached to an end of each of the first and second pubic arms. The support body has a body length extending between a first edge of the implant that is coincident with the transverse arms to a second edge of the implant located between the first and second pubic arms. Each of the first and second pubic arms has an arm length extending from the second edge of the implant to the end of the pubic arm and the arm length is less than the body length of the support body.

One aspect provides a method of treating urinary incontinence including forming a first incision exposing urethral tissue, and inserting an arm of a support into the first incision and penetrating an obturator foramen with the arm of the support. The method includes inserting a pubic arm of the support into the first incision without making a separate incision for placement of the pubic arm. The method additionally includes fixating the pubic arm by securing a separate pubic arm attachment mechanism that is fixed to an end of the pubic arm to tissue that is located lateral to the pubic symphysis.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
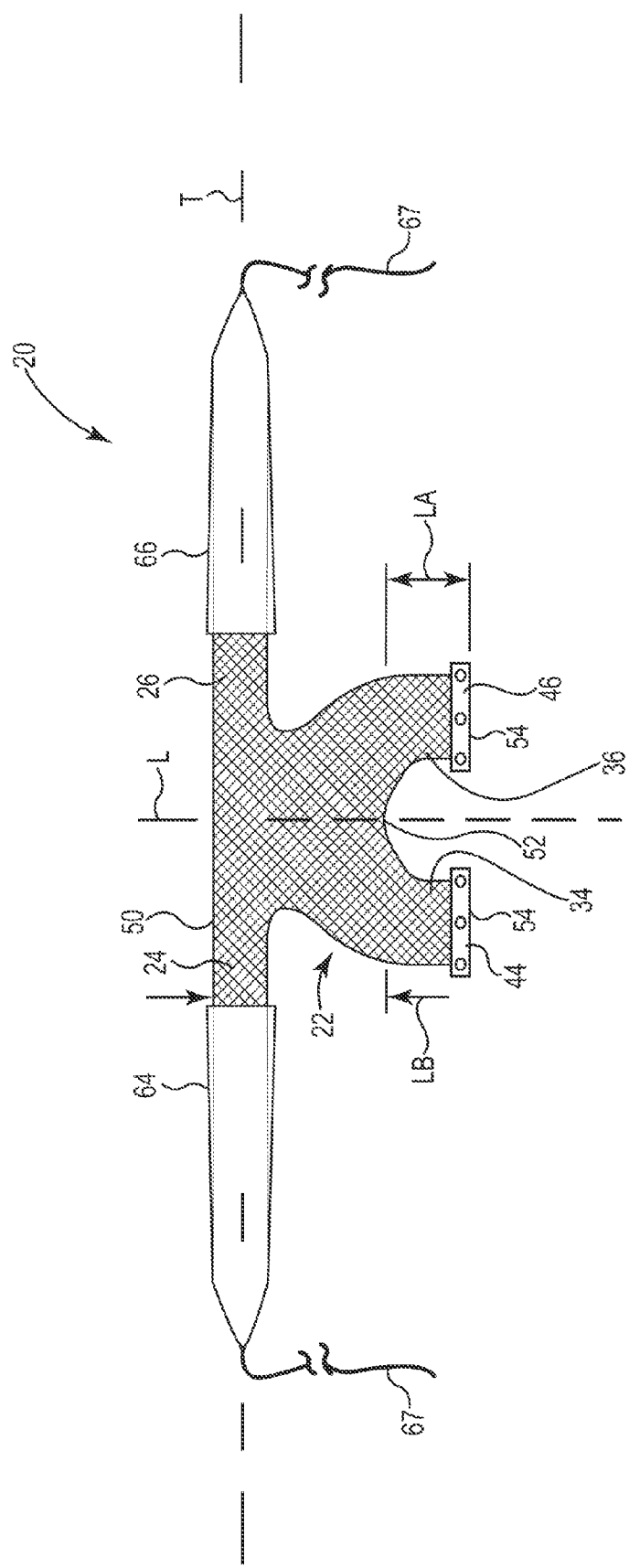
FIG. 1 is a top view of one embodiment of an implant adapted to treat urinary incontinence including a pubic arm attachment mechanism attached to each pubic arm.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

People suffering from urinary incontinence have a diminished ability to restrict the flow of urine through the urethra, usually due to a damaged or deficient urethral sphincter. The urethral sphincter is a collection of muscles that control the flow of urine from the bladder. These muscles envelop the urethra, and when contracted, seal the urethra shut. In general terms, each person has two urethral sphincters: an internal sphincter muscle of the urethra and an external sphincter muscle of the urethra. The internal sphincter muscle of the urethra is located near the junction of the urethra and the bladder. The external sphincter muscle of the urethra is located at the distal inferior end of the bladder in females and inferior to the prostate (at the level of the membranous urethra) in males.

The urethra is normally supported by connective and other tissues. The support provided by the connective tissues to the urethra can erode over time, giving rise to hyper-mobility of the urethra. Hyper-mobile urethras are susceptible to the undesirable leaking of urine during provocative events such as sneezing, laughing, or coughing (which is sometimes referred to as stress urinary incontinence).

The implant described herein is adapted to treat urinary incontinence and includes pubic arms that are shorter than a length of the support body of the implant. The shortened pubic arms each include an attachment mechanism that allows the pubic arms to be placed/implanted/fixed to the patient without making a separate incision for placement of the pubic arms. For example, pubic arms are typically placed by an instrument that is inserted into the skin of the abdomen above the pubic bone, and the instrument is tunneled anterior to the pubic bone in a "pre-pubic" or "supra-pubic" approach until the instrument exits an incision between the anus and the penis. In contrast, the implant described in this specification allows the pubic arms to be implanted and fixed in place without forming a separate skin access site. The implant described in this specification can be implanted through a single incision through which the support and the arms of the implant are passed prior to fixing the arms to tissue or other support structures.

FIG. 1 is a top view of one embodiment of an implant 20 adapted to treat urinary incontinence. The implant 20 includes a support body 22 defining a longitudinal axis L, two transverse arms 24, 26, two pubic arms 34, 36, and a pubic arm attachment mechanism 44, 46, respectively, for each pubic arm 34, 36.

The two transverse arms include a first arm 24 extending from the support body 22 transverse to the longitudinal axis L and a second arm 26 extending from the support body 22 in a direction opposite the first arm 24 and transverse to the longitudinal axis L such that the first and second arms 24, 26 provide transverse arms that are aligned on a common transverse axis T of the implant.

The two pubic arms include a first pubic arm 34 extending from the support body 22 and a second pubic arm 36 extending from the support body 22, with the first pubic arm 34 spaced a distance apart from the second pubic arm 36 and both the first and second pubic arms oriented parallel to the longitudinal axis L.

The pubic arm attachment mechanisms 44, 46 are each attached to an end of a respective one of the first and second pubic arms 34, 36.

The support body 22 has a body length LB extending between a first edge 50 of the implant 20 that is coincident with the transverse arms 24, 26 to a second edge 52 of the implant located at a midpoint between the first and second pubic arms 34, 36. Each of the first and second pubic arms 34, 36 has an arm length LA extending from the second edge 52 of the implant 20 to the ends 54 of the pubic arms 34, 36. In one embodiment, the arm length LA is less than the body length LB of the support body 22.

In one embodiment, the arms 24, 26 are provided as trans-obturator arms and each include an optional and removable insertion sheath 64, 66, respectively, and a suture 67 attached to the end of each arm 24, 26 and its respective insertion sheath 64, 66. During implantation of the implant 20 an introducer tool is utilized to separately engage each suture 67 and sequentially pass the first and second arms 24, 26 through a respective one of the first and second obturator foramen of the patient, as described below. The trans-obturator arms 24, 26 are passed through the obturator foramen of the patient, and the insertion sheaths 64, 66 are provided to allow the arms 24, 26 to pass through the tissue of the obturator foramen in a way that reduces the curling of the edges of the arms 24, 26. The insertion sheaths 64, 66 and the suture 67 are removable from the arms 24, 26 after the implant 20 is implanted. The suture 67 is provided to permit the tool to guide the arms 24, 26 and the insertion sheath 64, 66, respectively, when implanting the implant 20.

In one embodiment, the implant 20 is provided as a synthetic suburethral sling configured to treat stress urinary incontinence and the support body 22 is fabricated from knitted, monofilament polypropylene. The structure of the implant 20 is configured to allow tissue in-growth through at least a portion of the support body 22 or the arms 24, 26, 34, 36.

In one embodiment, the support body 22 is porous (having a plurality of pores or openings) and is fabricated from a knitted or woven or nonwoven mesh material. In one embodiment, the arms 24, 26 and 34, 36 are integrally formed with the support body 22 such that the support body 22 and the arms 24, 26 and 34, 36 are fabricated from a single unitary piece of material. In one embodiment, the support body 22 and the arms 24, 26 and 34, 36 are fabricated from a flexible knit mesh. In one embodiment, this single unitary piece of material is a porous polymer mesh. In one embodiment, the arms 24, 26 and 34, 36 are separately attached to the support body 22 and are fabricated from a material that is different than the support body 22.

In one embodiment, the insertion sheaths 64, 66 are provided as smooth polymer films and are fabricated in a flattened tubular structure and so configured to be removably placed over each of the arms 24, 26, respectively. The insertion sheaths 64, 66 are suitably fabricated from a polyolefin, such as polyethylene of polypropylene.

The sutures 67 are suitably selected from thermoplastic sutures, non-thermoplastic sutures, multi-filament sutures, or mono-filament sutures. In one embodiment, the sutures 67 are polypropylene sutures.

Figure 2:
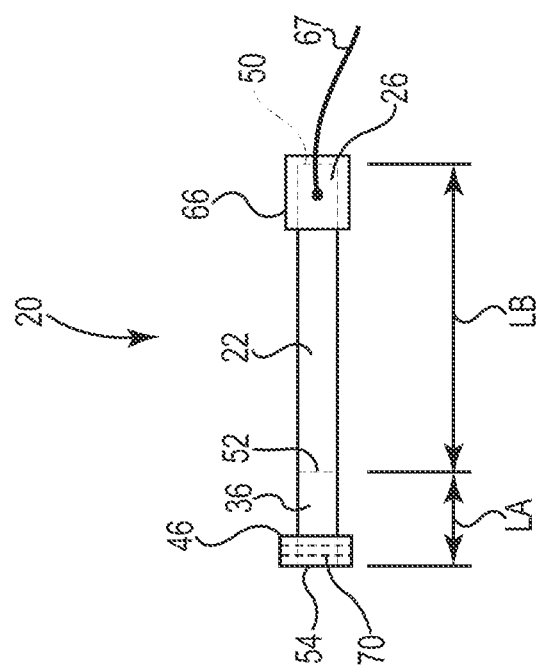
FIG. 2 is a side view of the implant illustrated in FIG. 1.

FIG. 2 is a right side view of the implant 20. The sheath 66 is disposed over the arm 26 and the pubic arm attachment mechanism 46 is attached to an end of the pubic arm 36. FIG. 2 illustrates that the arm length LA of the pubic arm 36 is less than the body length LB of the support body 22.

In one embodiment, the pubic arm attachment mechanism 46 is provided as a separate plastic clip that is attached over the end of the pubic arm 36 and is provided with at least one through-hole 70. In one embodiment, the clip is rigid and inflexible. In one embodiment, the clip is flexible and formed of a compliant material such as silicone, or silicone rubber, or rubber, or a rubber-like material. With reference to FIG. 1, each of the pubic arm attachment mechanisms 44, 46 is provided with three through-holes 70, although it is to be understood that the number of through-holes 70 can range from one through-hole to four or more or several through-holes. The through-holes 70 are configured to receive suture that allows the pubic arm attachment mechanisms 44, 46 to be attached to tissue, for example periosteum tissue of the pubic bone.

In one embodiment, the pubic arm attachment mechanism 46 is injection molded over the end of the pubic arm 36. In one embodiment, the pubic arm attachment mechanism 46 is a clam-shaped clip that is attached to the end of the pubic arm 36. The pubic arm attachment mechanism 46 may not align exactly with the end of the pubic arm 36, however the length of the pubic arm 36 and the length of the pubic arm attachment mechanism 46 combine to form a length that is less than the body length LB of the support body 22.

Figure 3:
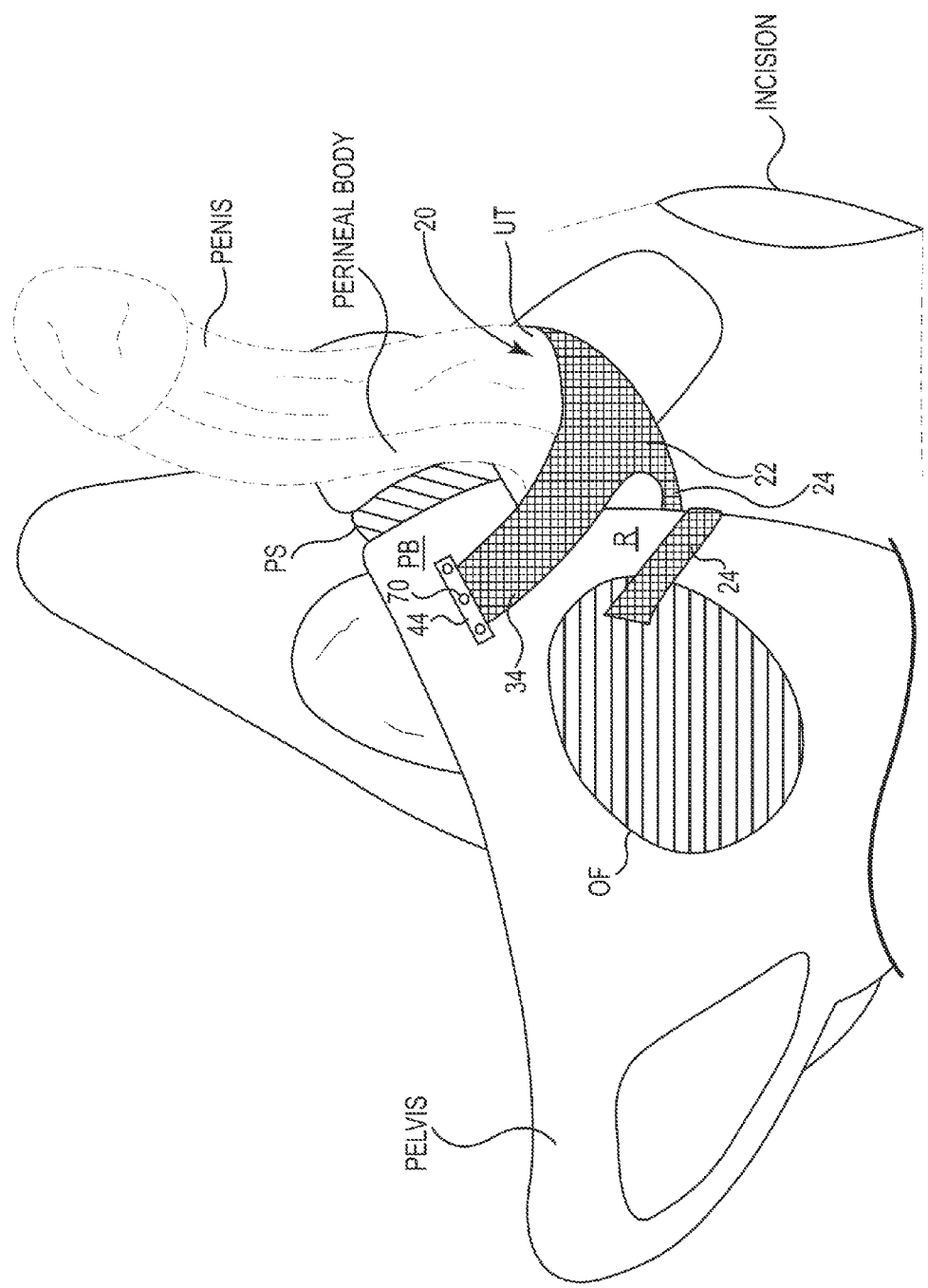
FIG. 3 is a perspective schematic view of the implant illustrated in FIG. 1 implanted in a male patient.

FIG. 3 is a perspective schematic view of the implant 20 implanted in a male patient. In general terms, a method of treating urinary incontinence includes: forming a first incision exposing urethral tissue UT; inserting an arm 24 of a support 20 into the first incision and penetrating an obturator foramen OF with the arm 24 of the support 20; inserting a pubic arm 34 of the support 20 into the first incision without making a separate incision for placement of the pubic arm 34; and fixating the pubic arm 34 by securing a separate pubic arm attachment mechanism 44 to tissue that is located lateral to the pubic symphysis PS.

Specific aspects of one suitable surgical procedure are described in the following paragraphs. The patient is typically placed in a dorsal lithotomy position with the legs positioned at about 90 degrees and held in place by stirrups. The patient is catheterized, for example with a 14 French catheter. The surgeon makes a vertical perineal incision in the midline and dissects tissue to eventually isolate the ventral bulbous urethra and pubic rami R while ensuring that the bulbospongiosus muscle around the urethra is intact. The surgeon will subsequently expose the bulbospongiosus muscle and take it off the perineal body to allow ventral urethral elevation compression by the support body 22.

The implant 20 is placed by engaging the suture 67 attached to each one of the trans-obturator arms 24, 26 with a suitable introducer tool and passing each of the arms 24, 26 through the perineal incision from the medial to the lateral through the obturator foramen in what has become known as an "inside-out" maneuver.

In one embodiment, each of the trans-obturator arms 24, 26 is individually introduced into the perineal incision by a curved introducer tool that directs each arm 24, 26 around the pubic ramus R until the suture 67 exits the perineal incision. In this manner, each arm 24, 26 is wrapped around a respective pubic ramus and the suture 67 enters and exits the perineal incision without forming a separate skin puncture for placement of the arms 24, 26.

In one embodiment, each of the pubic arms 34, 36 is individually introduced into the perineal incision and the pubic arm attachment mechanism 44 is attached to tissue on a left lateral side of the pubic symphysis PS and the pubic arm attachment mechanism 46 is attached to tissue on a right lateral side of the pubic symphysis PS. In one embodiment, the pubic arm attachment mechanisms 44, 46 are attached to the periosteum tissue of the pubic bone PB. In this manner, the pubic arms 34, 36 are placed through a single incision (the one perineal incision) without forming a separate skin puncture for placement of the arms 34, 36. That is to say, embodiments provide placement of the entire implant 20 through a single incision. The single incision may be a perineal incision as described above, or alternatively, the single incision may be a scrotal incision as described below.

Figure 4:
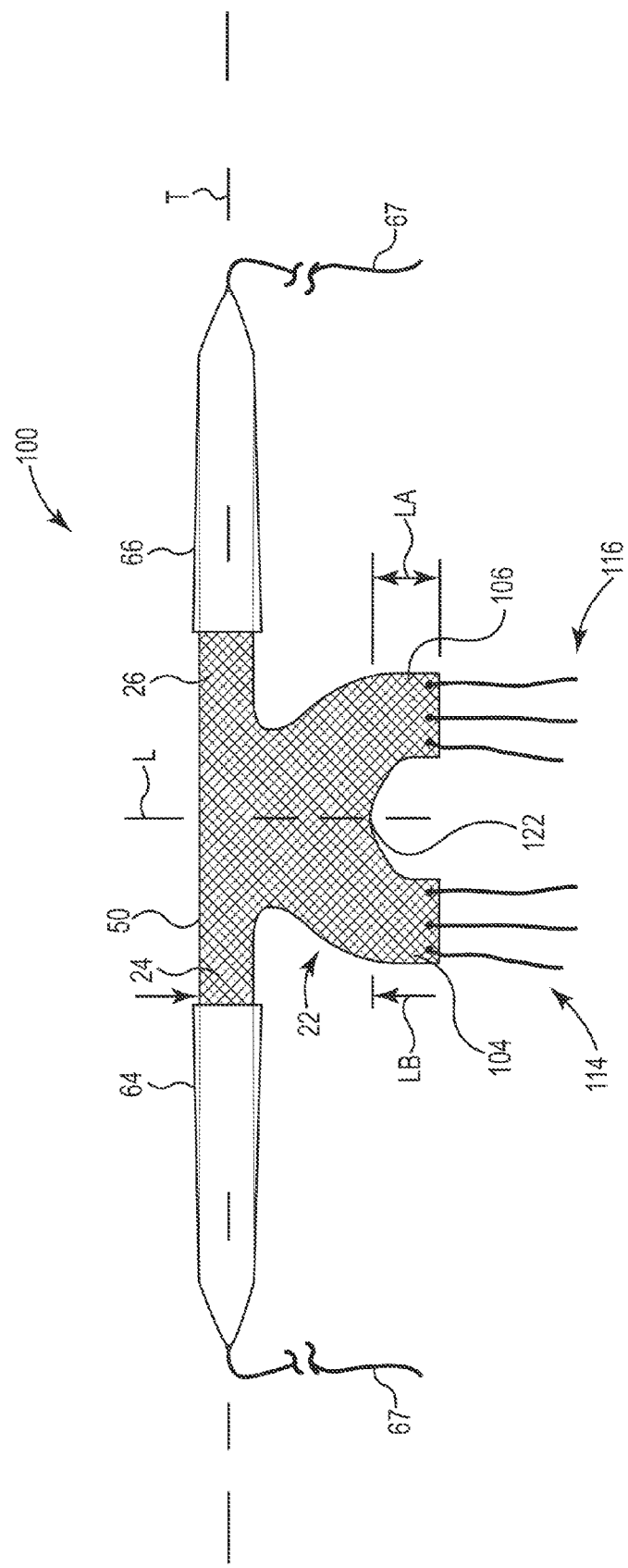
FIG. 4 is a top view of one embodiment of an implant adapted to treat urinary incontinence including a pubic arm attachment mechanism attached to each pubic arm.
Figure 5:
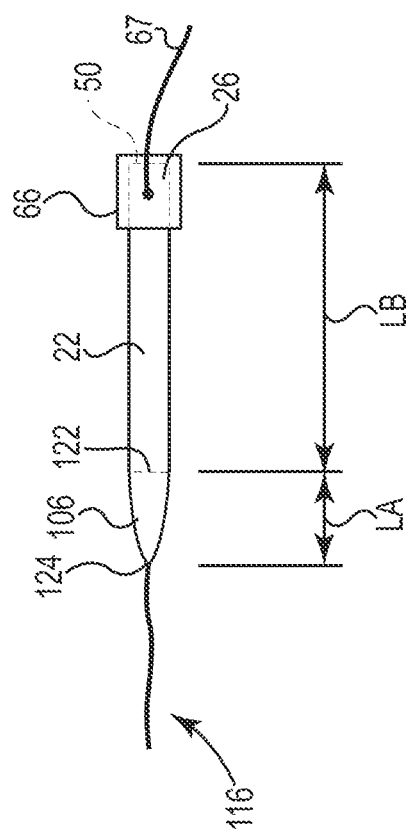
FIG. 5 is a side view of the implant illustrated in FIG. 4.

FIG. 4 is a top view and FIG. 5 is a right side view of one embodiment of an implant 100 adapted to treat urinary incontinence. The implant 100 includes the support body 22 described above defining the longitudinal axis L, the two transverse arms 24, 26 described above, two pubic arms 104, 106, and a pubic arm attachment mechanism 114, 116 for each pubic arm 104, 106.

The two transverse arms 24, 26 extend from the support body 22 transverse to the longitudinal axis L and are aligned on a common transverse axis T of the implant.

The two pubic arms 104, 106 extend from the support body 22, with the first pubic arm 104 spaced a distance apart from the second pubic arm 106 and both the first and second pubic arms oriented parallel to the longitudinal axis L.

The pubic arm attachment mechanisms 114, 116 are each attached to an end of a respective one of the first and second pubic arms 104, 106. In one embodiment, the pubic arm attachment mechanisms 114, 116 are provided as a plurality of pre-attached sutures stitched into an end of each of the pubic arms 104, 106. The stitching of the sutures of the attachment mechanisms 114, 116 reinforce and strengthen the ends of the first and second pubic arms 104, 106.

The support body 22 has a body length LB extending between the first edge 50 of the implant 100 that is coincident with the transverse arms 24, 26 to a second edge 122 of the implant 100 located at a midpoint between the first and second pubic arms 104, 106. Each of the first and second pubic arms 104, 106 has an arm length LA extending from the second edge 122 of the implant 100 to the ends 124 of the pubic arms 104, 106. In one embodiment, the arm length LA is less than the body length LB of the support body 22. In one embodiment, the length of the pubic arms 104, 106 and the length of the pubic arm attachment mechanisms 114, 116, respectively, combine to form a length that is less than the body length LB of the support body 22.

Figure 6:
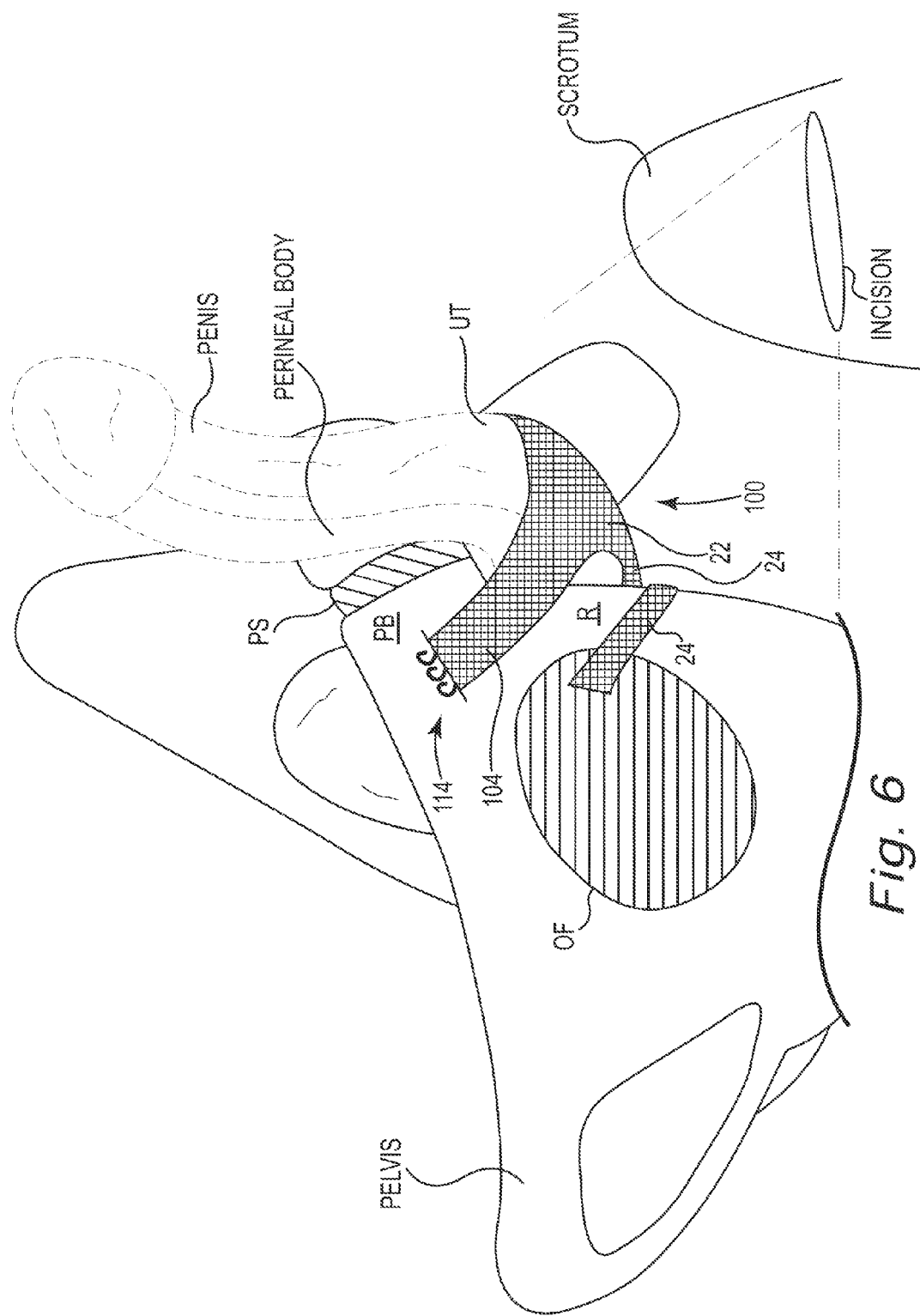
FIG. 6 is a perspective schematic view of the implant illustrated in FIG. 4 implanted in a male patient.

FIG. 6 is a perspective schematic view of the implant 100 implanted in a male patient Implantation of the implant 100 is similar to the procedure described above. The patient is typically placed in the dorsal lithotomy position with the legs positioned at about 90 degrees and held in place by stirrups. The patient is catheterized and the surgeon makes an incision, for example, a scrotal incision as illustrated. The surgeon dissects tissue to eventually isolate the ventral bulbous urethra and pubic rami R while ensuring that the bulbospongiosus muscle around the urethra is intact. The surgeon will subsequently expose the bulbospongiosus muscle and take it off the perineal body to allow ventral urethral elevation compression by the support body 22.

The implant 100 is placed by engaging the suture 67 attached to each one of the trans-obturator arms 24, 26 to a suitable introducer and passing each of the arms 24, 26 through the scrotal incision from the medial to the lateral through the obturator foramen taking care to avoid all nerve bundles.

In one embodiment, each of the trans-obturator arms 24, 26 is individually introduced into the scrotal incision by a curved introducer tool that directs each arm 24, 26 around the pubic ramus R until the suture 67 exits the scrotal incision. In this manner, each arm 24, 26 is wrapped around a respective pubic ramus and the trans-obturator arms 24, 26 are placed through the scrotal incision without forming a separate skin puncture for placement of the arms 24, 26.

In one embodiment, each of the pubic arms 104, 106 is individually introduced into the scrotal incision and the sutures of the pubic arm attachment mechanism 114 are attached to tissue on a left lateral side of the pubic symphysis PS and the sutures of the pubic arm attachment mechanism 116 are attached to tissue on a right lateral side of the pubic symphysis PS. In one embodiment, the pubic arm attachment mechanisms 114, 116 are attached to the periosteum tissue of the pubic bone PB lateral to the pubic symphysis PS. In this manner, the pubic arms 104, 106 are placed through a single incision (the one scrotal incision) without forming a separate skin puncture for placement of the arms 104, 106. That is to say, embodiments provide placement of the entire implant 100 through a single incision. The single incision may be a perineal incision as described above in FIG. 3, or alternatively, the single incision may be a scrotal incision as described here in FIG. 6.

Figure 7:
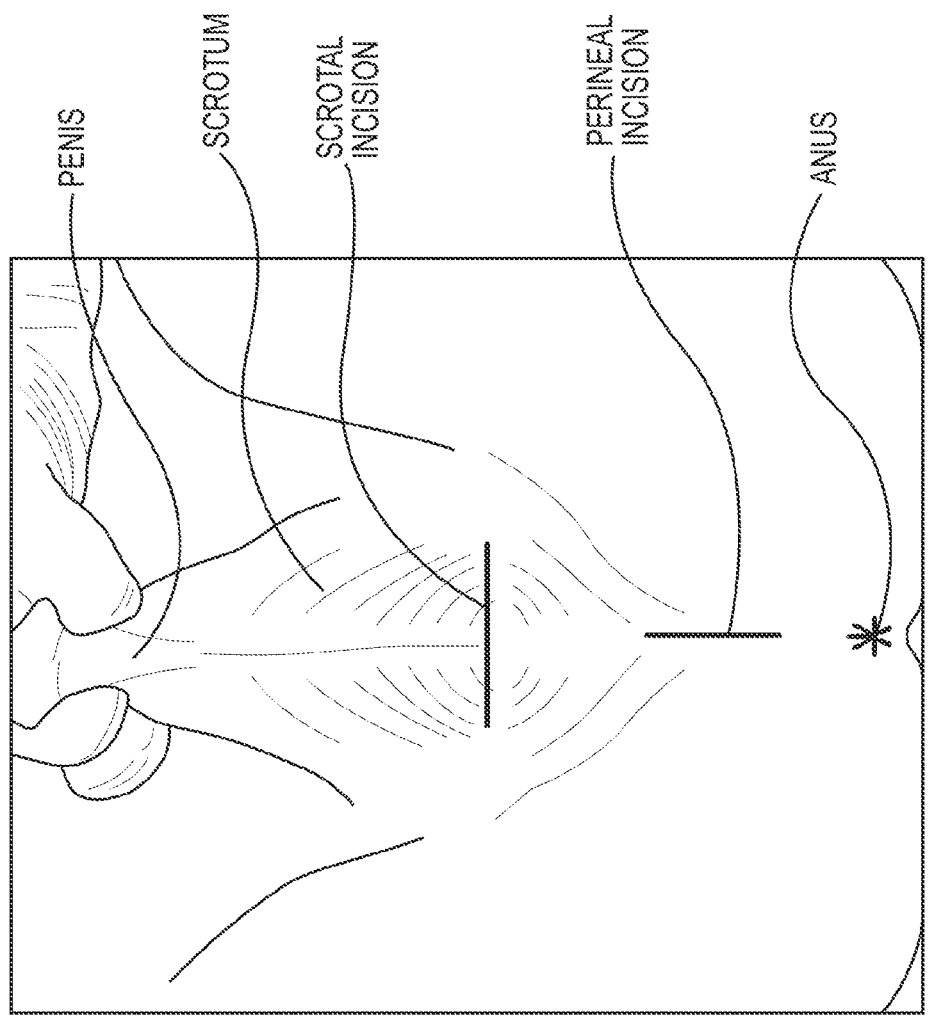
FIG. 7 is a front view illustrating a location of a perineal incision and a separate different location of a scrotal incision useful when implanting various embodiments of the implant described in this specification.

FIG. 7 illustrates a location for a scrotal incision and a separate location for a perineal incision. Embodiments of the implants described above are consistent with implantation through either a single scrotal incision or a single perineal incision.

Regarding the selection of the scrotal incision for implantation of an implant described above, the penis and the scrotum are moved cephalad and held in place by tape or a retractor. The scrotal incision is formed at the base of the scrotum laterally relative to the midline of the patient.

Regarding the selection of the perineal incision for implantation of an implant described above, the penis and the scrotum are moved cephalad and the perineal incision is formed between the anus and the scrotum on the midline of the patient.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A method of treating male urinary incontinence, the method comprising:
    forming a first incision exposing urethral tissue;
    inserting a first trans-obturator arm of a support into the first incision and penetrating an obturator foramen with the first trans-obturator arm of the support, the support including a support body having a longitudinal axis and a lateral axis, the first trans-obturator arm extending from the support body in a direction of the lateral axis of the support body and a second trans-obturator arm extending from the support body opposite the first trans-obturator arm;
    inserting the second trans-obturator arm of the support into the first incision and penetrating an obturator foramen with the second trans-obturator arm of the support that is opposite the obturator foramen into which the first trans-obturator arm is penetrated;
    inserting a first pubic arm of the support into the first incision without making a separate incision for placement of the first pubic arm, the support including a second pubic arm, the first and second pubic arms extending from the support body substantially in a direction of the longitudinal axis of the support body, the first pubic arm laterally spaced from the second pubic arm, the support body having a body length between a first edge of the support that is coincident with the first and second trans-obturator arms to a second edge of the support coincident with an edge of the body located between the first and second pubic arms, each of the first and second pubic arms having an arm length extending from the second edge of the support to the ends of the first and second pubic arms, respectively, the arm length of each of the first and second pubic arms being less than the body length;
    fixating the first pubic arm by securing a pubic arm attachment mechanism of the first pubic arm that is fixed to an end of the first pubic arm to periosteum tissue that is located lateral to the pubic symphysis;
    inserting the second pubic arm into the first incision; and
    fixating the second pubic arm by securing a pubic arm attachment mechanism of the second pubic arm to tissue that is located lateral to the pubic symphysis and on an opposite side of the pubic symphysis to which the first pubic arm is attached.

2. The method of claim 1, wherein the pubic arm attachment mechanism of the first pubic arm comprises a plastic clip defining an array of holes, the plastic clip attached to the end of the pubic arm, the method further comprising:
    placing a suture in the tissue that is located lateral to the urethral tissue;
    inserting the suture into at least one hole in the array of holes; and
    tying the suture to the pubic arm attachment mechanism of the first pubic arm.

3. The method of claim 1, wherein the pubic arm attachment mechanism of the first pubic arm includes a plurality of sutures extending from the pubic arm attachment mechanism of the first pubic arm, the method further comprising:
    securing at least one of the plurality of sutures to the tissue that is located lateral to the urethral tissue.

4. The method of claim 1, wherein forming a first incision exposing urethral tissue comprises forming only one incision.

5. The method of claim 1, wherein forming a first incision exposing urethral tissue comprises forming a perineal incision exposing urethral tissue.

6. The method of claim 1, wherein forming a first incision exposing urethral tissue comprises forming a single scrotal incision exposing urethral tissue.

7. The method of claim 1, wherein the first incision is the only incision formed to expose urethral tissue.

8. The method of claim 7, wherein inserting the first trans-obturator arm of the support into the one incision and penetrating the obturator foramen comprises:
    introducing the first trans-obturator arm of the support into the one incision with a tool;
    penetrating the obturator foramen with the tool;
    passing an end of the first trans-obturator arm around a ramus with the tool; and
    directing the end of the first trans-obturator arm around the ramus and out of the one incision.

9. The method of claim 7, wherein inserting a first pubic arm of the support into the first incision comprises inserting the first pubic arm of the support into the one incision and fixating the first pubic arm comprises securing the pubic arm attachment mechanism fixed to the end of the first pubic arm to periosteum tissue of the pubic bone.

10. A method of treating male urinary incontinence in a patient, the method comprising:
    providing a support comprising:
        a body defining a longitudinal axis and a lateral axis;
        a first and a second pubic arm, the first pubic arm extending from the body in a direction of the longitudinal axis, and the second pubic arm laterally spaced from the first pubic arm and extending from the body in a direction of the longitudinal axis; and
        a first and a second trans-obturator arm, the first trans-obturator arm extending from the body in a direction of the lateral axis, and the second trans-obturator arm extending from the body opposite the first trans-obturator arm;
        wherein the body has a body length between a first edge of the support that is coincident with the trans-obturator arms to a second edge of the support coincident with an edge of the body located between the first and second pubic arms, and each of the first and second pubic arms having an arm length extending from the second edge of the support to the ends of the first and second pubic arms, respectively, the arm length being less than the body length;
    forming only one incision in the patient and exposing urethral tissue;
    inserting the first trans-obturator arm of the support into the one incision and penetrating an obturator foramen of the patient with the first trans-obturator arm;
    inserting the second trans-obturator arm of the support into the one incision and penetrating an obturator foramen of the patient with the second trans-obturator arm;
    inserting the first pubic arm of the support into the one incision;
    inserting the second pubic arm of the support into the one incision; and fixating the first and second pubic arms by securing a first and a second pubic arm attachment mechanisms of the first and second pubic arms to opposite locations lateral to the pubic symphysis.

11. The method of claim 10, wherein forming only one incision in the patient and exposing urethral tissue comprises forming a scrotal incision in the patient and exposing urethral tissue.

12. The method of claim 10, further comprising:
passing an end of each of the first and the second trans-obturator arms around a ramus of the patient; and
directing the end of each of the first and the second trans-obturator arms around the ramus and out of the one incision.

13. The method of claim 10, wherein the pubic arm attachment mechanisms define an array of holes, the method further comprising:
placing a suture in periosteum tissue;
inserting the suture into at least one hole in the array of holes; and
tying the suture to one of the pubic arm attachment mechanisms.

14. The method of claim 10, wherein the pubic arm attachment mechanisms include a plurality of sutures extending from the pubic arm attachment mechanism, the method further comprising:
securing at least one of the plurality of sutures to periosteum tissue.

15. A method of treating male urinary incontinence, the method comprising:
forming an incision exposing urethral tissue;
inserting a first pubic arm of a support into the incision without making a separate incision for placement of the first pubic arm, the first pubic arm extending from a support body defining a longitudinal axis and a lateral axis, the first pubic arm extending from the support body in a direction of the longitudinal axis and a second pubic arm extending from the support body in the direction of the longitudinal axis of the support body, the first pubic arm being laterally spaced from the second pubic arm, an arm length of each of the first and the second pubic arms being less than a body length of the support body;
fixating the first pubic arm to tissue located lateral to the pubic symphysis;
inserting a first trans-obturator arm of the support into the incision, the first trans-obturator arm extending from the support body in a direction of the lateral axis and a second trans-obturator arm extending from the support body in the direction of the lateral axis and opposite to the first trans-obturator arm; and
penetrating an obturator foramen with the first trans-obturator arm.

16. The method of claim 15, further comprising:
inserting the first pubic arms of the support into the incision without making a separate skin puncture for placement of the first pubic arm; and
fixating the first pubic arm by securing a first pubic arm attachment mechanism that is fixed to an end of the first pubic arm to periosteum tissue of a pubic bone of the patient that is located lateral to the pubic symphysis.

17. The method of claim 16, further comprising:
passing an end of the first trans-obturator arm around a ramus of the patient; and
directing the end of the first trans-obturator arms around the ramus and out of the incision.

18. The method of claim 16, wherein the incision is formed in the scrotum of the patient.

19. The method of claim 16, wherein the incision is a non-scrotal incision formed in the perineum of the patient.

20. The method of claim 16, wherein the first pubic arm attachment mechanism comprises a plastic strip that is fixed across a width of the pubic arm and configured to distribute stress across the width of the pubic arm.

* * * * *